United States Patent
Yaacobi

[11] Patent Number: 5,860,994
[45] Date of Patent: Jan. 19, 1999

[54] REMOTELY OPERABLE INTRAOCULAR SURGICAL INSTRUMENT FOR AUTOMATED CAPSULECTOMIES

[76] Inventor: Yoseph Yaacobi, 2509 Kelton St., Fort Worth, Tex. 76133

[21] Appl. No.: 688,498

[22] Filed: Jul. 30, 1996

[51] Int. Cl.[6] .............................. A61F 09/00; A61B 17/32
[52] U.S. Cl. ............................................ 606/166; 167/107
[58] Field of Search .............................. 606/1, 159, 166, 606/167, 170, 171, 180, 107

[56] References Cited

U.S. PATENT DOCUMENTS

| | | |
|---|---|---|
| 3,908,661 | 9/1975 | Kramer . |
| 4,530,359 | 7/1985 | Helfgott et al. . |
| 4,672,965 | 6/1987 | Baum . |
| 4,676,243 | 6/1987 | Clayman . |
| 4,708,138 | 11/1987 | Pazandak . |
| 4,766,897 | 8/1988 | Smirmaul . |
| 4,911,161 | 3/1990 | Schechter . |
| 5,156,607 | 10/1992 | Kansas . |
| 5,167,618 | 12/1992 | Kershner . |
| 5,261,923 | 11/1993 | Soares . |
| 5,269,787 | 12/1993 | Cozean, Jr. et al. . |
| 5,342,377 | 8/1994 | Lazerson . |
| 5,423,841 | 6/1995 | Kornefeld . |
| 5,496,339 | 3/1996 | Koepnick ............................. 606/166 |

FOREIGN PATENT DOCUMENTS

| | | |
|---|---|---|
| 0 165 657 | 12/1989 | European Pat. Off. . |
| PCT/US93/ 03702 | 10/1993 | WIPO . |

*Primary Examiner*—Glenn K. Dawson
*Attorney, Agent, or Firm*—J. Kevin Gray, Esq.

[57] ABSTRACT

A remotely operable intraocular surgical instrument specially adapted to perform anterior capsulectomy/capsulorhexis for extracapsular cataract extractions and emulsifications is disclosed. The intraocular instrument has a main body portion including at least two internally defined passageways and a rounded internal chamber including a rotatable wheel or a gear. An arm of variable length including a knife is associated with the rotatable wheel or gear such that movement of the wheel/gear rotates the knife through 360 degrees. In one embodiment, the wheel is driven through the use of a fluid forced through the internal passageways and around the wheel. In another embodiment a shaft having specialized teeth communicates pressure applied to a handle to the gear, thus turning the associated knife. Both embodiments include a releasable stop to prevent the knife from rotating and cutting past 360 degrees. Both embodiments also include structure for providing a viscoelastic solution to the operative field and an optional passageway to remove undesired material from the operative field. The lack of movement of the main body portion of the instrument during the procedure, simplicity of design, relative low expense of manufacture and disposable nature of the instrument provide obvious advantages and benefits.

17 Claims, 4 Drawing Sheets

REMOTELY OPERABLE INTRAOCULAR SURGICAL INSTRUMENT FOR AUTOMATED CAPSULECTOMIES

BACKGROUND OF THE INVENTION

Among other factors, vision depends upon the transparency of an individual's lens. The lens, encapsulated by a cellophane-like membrane covering its anterior and posterior surfaces, focuses light entering the eye onto the retina. Opacity or cloudiness of the lens may prevent a clear image from forming on the retina. This condition, commonly known as a cataract, may be congenital or result from trauma, disease or age. When visual loss reaches a certain point, the lens may be removed and replaced by an intraocular lens.

Various techniques and procedures have been developed to remove a cataract. In perhaps the most popular technique, known as an extracapsular extraction procedure ("ECCE"), the anterior capsule is opened and the lens extracted and replaced. Opening the anterior capsule via an anterior capsulectomy is a very delicate procedure and is widely considered to be the most difficult step in an ECCE. Complications, including zonular stress, vitreous loss, large capsular tags, and difficulties in nucleus expression are unfortunately frequent, causing increased operative duration and frequency as well as pain and discomfort for the patient. A more thorough review of various procedures and their associated complications is found in *Phacoemulsification and Aspiration of Cataracts*, Chapter 10 (1979)(Emery, J. M. and Little, J. H. eds.), incorporated herein by reference.

A variety of devices have been developed to cut or tear the anterior capsule to facilitate removal of the lens. Perhaps the most common device is a cystotome. When cataracts are removed by an ECCE, a cystotome is inserted through a small incision in the sclera or peripheral cornea and small connecting tears are made in the anterior lens capsule in a circular pattern around the periphery of the lens capsule. The tears are subsequently connected to form a complete circle. The resulting circular piece of the anterior capsule is then removed and the lens extracted.

The phacoemulsification method of cataract removal requires a different type of anterior capsular opening. During phacoemulsification, there is a great deal of tension on the cut edges of the anterior capsule while the lens nucleus is emulsified with ultrasound energy. Accordingly, for this method, a tagless, continuous cut or tear is a critical step for safe and effective phacoemulsification. If the capsule is opened with numerous small capsular tears, as in the above-described extracapsular technique, the small tags which remain can lead to capsular tears which may extend posteriorly to the posterior capsule. Such a radial tear constitutes a complication since it destabilizes the lens for further cataract removal and safe intraocular lens placement within the lens capsule later in the operation. More importantly, once the posterior capsule is punctured, the vitreous humor behind it gains access to the front of the eye. If the vitreous enters the front of the eye through a hole in the posterior capsule, the vitreous must be removed by an additional procedure with special instruments. The loss of vitreous also is associated with an increased rate of subsequent retinal detachment and/or infection within the eye. Importantly, these complications are potentially blinding.

In addition to the above-identified complications with extracapsular extractions and phacoemulsification, several other disadvantages are associated with the devices and methods employed for the procedures. Prior art devices and methods used to produce a continuous curvilinear capsular opening require extraordinary skill and technique by the surgeon performing the operation. This is due to the extreme difficulty in controlling the path of the device.

For example, the most typical method begins with a capsular incision made with a cystotome. This incision is then coaxed to form a circular or oval shape by pushing the leading edge of the freshly tearing capsule with the cystotome in a non-cutting fashion. Alternatively, the initial capsular incision is torn into a circular shape by grasping the leading edge with fine caliber forceps and advancing the cut in a very uncontrolled manner. This is a very challenging maneuver and, even in the most experienced hands, the tearing motion can lead to an undesirable tear of the capsule toward the back of the lens. Moreover, even if a tagless edge is ultimately produced, the size and/or position of the capsular opening presents a problem. For example, a small capsular opening can impair the safe removal of the lens nucleus and cortex and prevent proper intraocular lens insertion into the lens capsule. The additional stresses necessary to accomplish the operation with a small or misplaced capsular opening put the eye at risk for zonular and capsular breakage. Both of these types of breakage will likely increase the length and complexity of the operation and can result in vitreous loss.

A continuous, properly positioned and circular opening is highly desirable since it results in: (1) a significant reduction in radial tears and tags within the anterior capsule, (2) capsule integrity necessary for proper centering of a lens prosthesis; (3) safe and effective hydrodissection; and (4) safe use of capsular procedures on patients having poorly visualized capsules and/or small pupil openings.

Prior devices employed in performing an anterior capsulectomy include manual and mechanical techniques for severing the anterior lens capsule of the eye. For example, U.S. Pat. No. 4,570,632 to Woods describes a cystotome which produces a continuous series of perforations. Additionally, U.S. Pat. No. 4,706,669 to Schlegel describes a device for perforating the lens capsule using a wire connected to a drive motor. A more recent device includes the use of a manually controlled rotating blade (U.S. Pat. No. 5,423,841 to Kornfeld).

In most prior known devices, it is difficult to cleanly cut the anterior capsule without leaving residual "tags" or tears in the capsule. Additionally, these devices either cause sufficient drag on the capsule and upset the nucleus of the lens, or place stress on the zonular structure. More importantly, most of these devices offer the surgeon little or no control over the exact placement of the cutting edge during the procedure and require exceptional skill and control to avert undesired results (e.g., tags, irregular cutting path, etc.). Finally, most of these devices do not provide a continuous, properly positioned, circular opening in the anterior capsule.

Most, if not all, of the problems associated with the above-described prior art devices and methods are produced because use of the instrument or device requires movement of the instrument (i.e., the instrument does not remain stationary during the procedure). Movement of the instrument (e.g., through positioning and re-positioning the instrument and during the actual cutting portion of the procedure) produces damage to surrounding tissue (e.g., the endothelium of the cornea). Such damage increases: (1) the length of the procedure, (2) pain to the patient; (3) the number of complications; and (4) the recovery time, and is virtually unavoidable by the surgeon using such devices since movement is required to accomplish the procedure. Accordingly, there remains a need for a remotely operable intraocular cutting instrument specifically adapted for capsulorehexis procedures and capable of producing a continuous, circular, smooth, stress-free, tag-free cut along the anterior capsule to facilitate removal of the lens during a capsulectomy and requiring virtually no movement of the instrument once position to accomplish the procedure.

SUMMARY OF THE INVENTION

The intraocular surgical instrument of the present invention overcomes the foregoing and other problems associated with the prior art by providing an intraocular instrument specifically adapted for capsulorehexis procedures and capable of producing a continuous, circular, smooth, stress-free, tag-free cut along the anterior capsule to facilitate removal of the lens during a capsulectomy. Importantly, the intraocular surgical instrument of the present invention requires virtually no movement of the instrument once positioned to accomplish the procedure.

The preferred embodiment of the intraocular surgical instrument comprises a main body portion, a rotating arm and associated knife, and one or more internal chambers capable of conducting a fluid through the main body portion and rotating the arm and associated knife through 360 degrees. In use, the arm and associated knife are rotated underneath and flush with the main body portion of the instrument and the instrument is slipped through a superior corneo-scleral incision. Once positioned, a point anchors the instrument in place for the remainder of the procedure. The surgeon remotely activates the flow of a fluid through the internal chamber(s) of the main body portion to rotate the arm and associated knife through 360 degrees. The arm is prevented from rotating past 360 degrees unless the surgeon desires such rotation and releases a stop. Once the cut is completed, the arm and knife are returned to the flush position with the main body portion and the instrument is removed from the operative field.

The intraocular surgical instrument of the present invention features a knife and anchor pin foldable between a first position and a second position so that, in the first position, the cutting edge of the knife and the sharpened point of the anchor pin rests flush with the main body of the instrument so as to prevent damage to surrounding tissue upon insertion and removal of the instrument. The knife and anchor pin are also stored in the first position during periods of nonuse for safety reasons. In the second position, the knife and the anchor pin extend perpendicularly to the plane of the main body of the instrument so that the sharpened point of the anchor pin and the cutting edge of the knife are available to anchor the main body of the instrument and cut, respectively, during use of the instrument.

In a different embodiment, rotation of the arm and the associated knife is accomplished using a rotatable gear and shaft located within the main body portion. The surgeon controls the rotatable gear via the shaft outside the operative field. A single depression of the shaft provides a full 360 degree rotation of the arm and associated knife, thus minimizing movement during the cutting procedure. Importantly, this feature again allows the arm and associated knife to rotate without communicating movement to the instrument, avoiding damage caused by such movement to the surrounding tissue.

The design of the arm and associated knife of the intraocular surgical instrument of the present invention provides excellent visual inspection of the operative field and the cut being made by the knife. The intraocular surgical instrument of the present invention also features the use of arms of various sizes, allowing the surgeon to customize the cutting diameter to the surgical needs (e.g., the size of the patient's eye).

Regardless of the embodiment, the intraocular surgical instrument of the present invention allows the surgeon to place and anchor the instrument and subsequently operate the instrument without moving the instrument. This feature provides a great benefit over the prior art since the lack of movement during the procedure precludes damage to surrounding tissue (e.g., endothelium of the cornea), thus reducing complications and decreasing pain and recovery time.

DESCRIPTION OF THE DRAWINGS

For a more complete understanding of the present invention and the advantages thereof, reference is now made to the following description taken in conjunction with the accompanying drawings in which.

DETAILED DESCRIPTION

Figure 1:
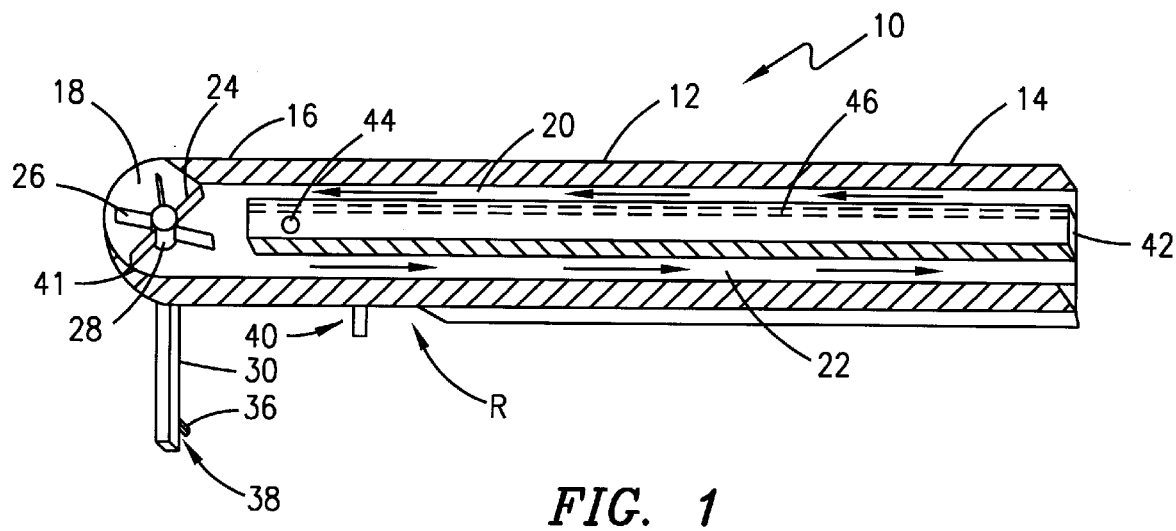
FIG. 1 is a perspective view, partially in section, of the preferred embodiment of the remotely operable intraocular surgical instrument of the present invention.

Referring to FIG. 1, there is shown a remotely operable intraocular surgical instrument of the present invention. In one preferred embodiment, the instrument 10 comprises a main body portion 12 with a proximal end 14 and a distal end 16. Located within the distal end 16 of the main body portion 12 is a generally rounded internal chamber 18. The exterior of the distal end 16 of the main body portion 12 is likewise generally rounded. Disposed within and running substantially the entire longitudinal length of the main body portion 12 of the instrument 10 are a first internally defined passageway 20 and a second internally defined passageway 22 which connect the proximal end 14 of the main body portion 12 and the rounded internal chamber 18 within the distal end 16 of the main body portion 12. The first passageway 20 and the second passageway 22 are connected to the rounded internal chamber 18 within the distal end 16 of the main body portion 12, forming a continuous pathway from the proximal end 14 through the main body portion 12 to the rounded internal chamber 18 and back through the main body portion 12 to the proximal end 14 of the main body portion 12 of the instrument 10.

Figure 2:
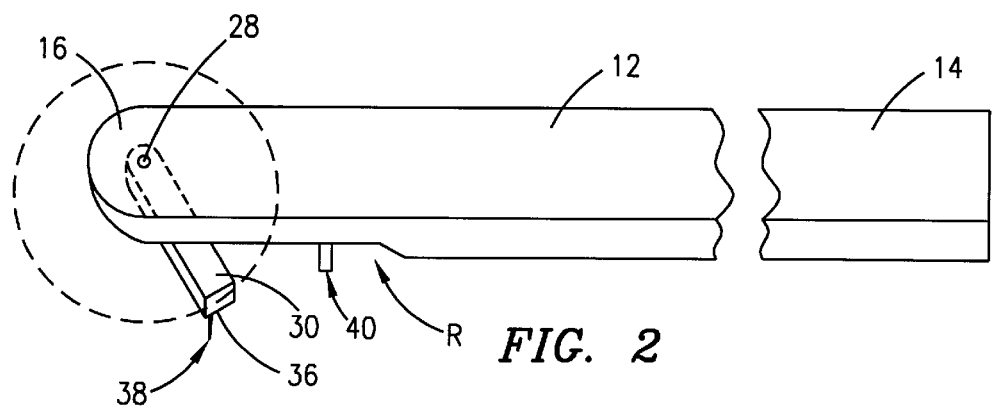
FIG. 2 is a top view of the preferred embodiment of the remotely operable intraocular surgical instrument of the present invention.
Figure 6:
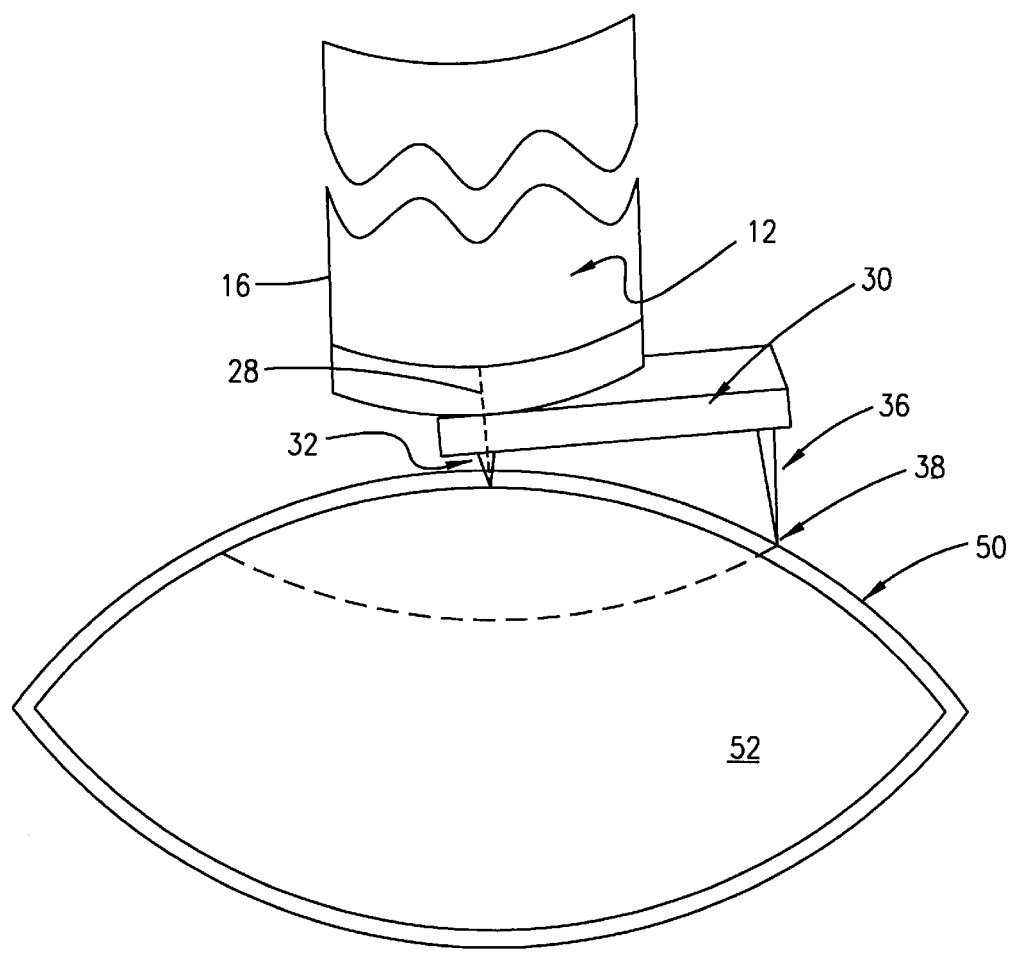
FIG. 6 is a perspective view of an embodiment of the remotely operable intraocular surgical instrument of the present invention in use on a human eye.

Within the rounded internal chamber 18 is located a rotating paddlewheel 24. The paddlewheel 24 is attached at its midpoint 26 to the lower surface of the rounded internal chamber 18 via an anchor pin 28 which extends through and below the main body portion 12 of the instrument 10. An arm 30 is attached to the lower end of the anchor pin 28. As illustrated in FIGS. 1, 2 and 6, the anchor pin 28, the paddlewheel 24 and the arm 30 are attached in a manner which allows them to rotate freely through 360 degrees. The lower surface of the distal end 16 of the main body portion 12 of the instrument 10 is recessed R such that the depth of the arm 30 plus the depth of the distal upper end of the main body portion 12 is substantially the same as the depth of the proximal end 14 of the main body portion 12 of the instrument 10. This feature allows the anchor pin 28 and arm 30 to be tucked up underneath the main body portion 12 of the instrument 10 during periods of nonuse, allowing the instrument 10 to be more easily inserted through a limbal incision during a capsulectomy. Referring to FIG. 6, the lower central end of the anchor pin 28 includes a slightly sharpened point 32 which, as will be explained in detail below, is used to position and anchor the instrument 10 in place during a capsulectomy.

Referring again to FIGS. 1, 2 and 6, a knife 36 is attached to the arm 30 such that the cutting edge 38 of the knife 36 extends slightly below the anchor pin 28. As will be explained in greater detail below, the slight increase in length of the knife 36 corresponds to the curvature of the surface to be cut (i.e., anterior capsule), allowing the cutting edge 38 of the knife 36 to properly contact and cut the surface of anterior capsule during a capsulectomy. A releasable stop 40 is located in the recessed area R to prevent the arm 30 from rotating more than 360 degrees and to lock the arm 30 into position within the recessed area R during periods of nonuse. As the arm 30 strikes the releasable stop 40, the paddlewheel 24 and associated cutting edge 38 of the knife 36 are prevented from further rotation. The releasable stop 40 can be released remotely by the surgeon in the event that an additional circular cutting is desired. Although a releasable stop 40 is described herein, it is noted that any suitable means of preventing the knife 36 and cutting edge 38 from rotating past 360 degrees can be used, if desired.

The anchor pin 28 and the knife 36 are foldable between a first position and a second position. In the first position, the anchor pin 28 and knife 36 are folded flat against the arm 30 so as to prevent damage during insertion and removal of the instrument 10. This is also the position preferred when the instrument 10 is not in use. In the second position, the anchor pin 28 and knife 36 extend perpendicularly from the plane of the arm 30. This is the position selected once the instrument 10 has been inserted through the limbal incision and is positioned for the procedure.

In the preferred embodiment, the knife 36 is clipped into place at the appropriate position on the arm 30. Although a clip fastening method is described herein, it is noted that any suitable method of securely attaching the knife 36 to the arm 30 may be used, if desired. Alternatively, particularly when the instrument 10 is disposable in nature, the instrument 10 can be manufactured with different lengths of arm 30 such that the appropriate instrument (having the desired cutting diameter) is selected prior to use of the instrument 10. This feature of the instrument 10 allows the surgeon to customize the cutting diameter to the surgical needs (e.g., size of patient's eye).

As indicated by arrows in FIG. 1, during use one or more fluids is/are directed through the first passageway 20 at the proximal end 14 of the main body portion 12 to activate the instrument 10. As the fluid passes through the first passageway 20, it enters the rounded internal chamber 18 and contacts the paddlewheel 24 on its path through the rounded internal chamber 18, turning the paddlewheel 24 and attached anchor pin 24, thus rotating the arm 30, the knife 36 and the cutting edge 38 below through 360 degrees. The fluid exits the rounded internal chamber 18 via second passageway 22 back to the proximal end 14 of the main body portion 12 and is either reused to drive the paddlewheel 24 or discarded. A fluid pumping system (not shown), such as a recirculation pump, the suitable types of which are known in the art, and including a foot pedal is used to remotely control the flow of fluid through the instrument. As used herein, "fluid" encompasses any flowable material, including without limitation, liquids and gases.

An optional central internally defined passageway 42 is located within the main body portion 12 of the instrument 10 and between passageways 20 and 22. Such central passageway 42 is closed at its distal end and is used to deliver a viscoelastic fluid via opening 44 to the operative field during a procedure. A second optional internally defined passageway 46 extending substantially the entire longitudinal length of the main body portion 12 is used to suction off the capsular membrane and undesired fluid, etc., from the operative field during a procedure. Control of the first and second optional passageways is preferably accomplished via the foot pedal associated with the fluid control system.

Figure 4:
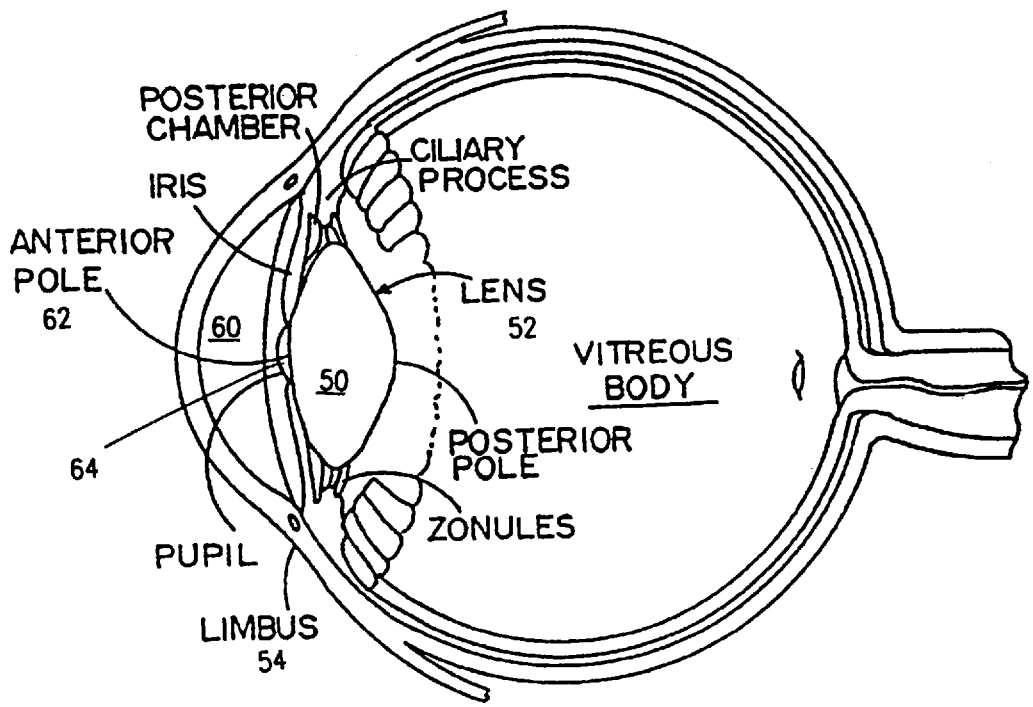
FIG. 4 is a side view of a human eye in cross section illustrating the major components associated with a capsulectomy.
Figure 5:
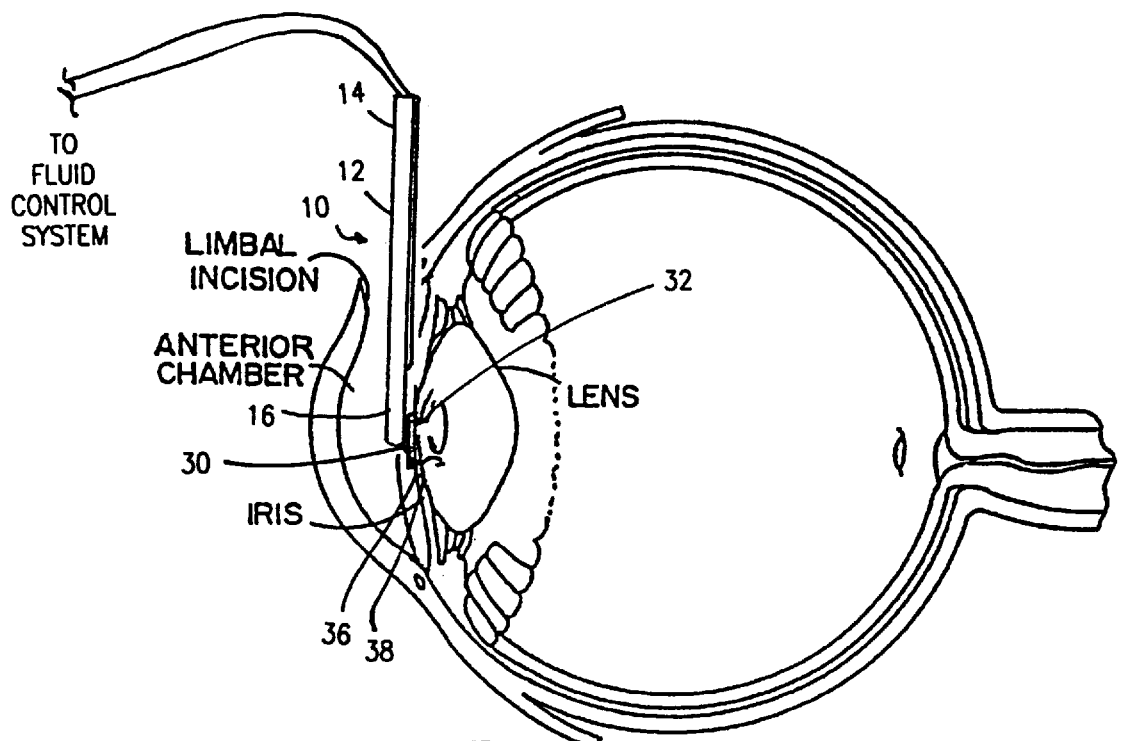
FIG. 5 is a side view of a human eye illustrating placement of an embodiment of the remotely operable intraocular surgical instrument of the present invention.

Now referring to FIGS. 4, 5 and 6, use of the remotely operable intraocular surgical instrument 10 of present invention to make a continuous, circular, smooth, stress-free, tag-free cut along the anterior capsule 50 to facilitate removal of the lens 52 during an extracapsular cataract extraction/emulsification is described. During an extracapsular cataract extraction/emulsification procedure, a superior corneo-scleral incision (approximately 4–7 mm in length) is made along the limbus 54. With the arm 30 rotated to rest under the main body portion 12 of the instrument 10, the instrument 10 is inserted into the anterior chamber 60 (FIG. 4) through the corneo-scleral incision such that the rounded internal chamber 18 of the instrument is positioned over and facing the anterior pole 62 of the capsule 64.

Next, the point 32 is centered over the anterior pole 60 (FIG. 6). Once centered, the instrument 10 is lowered towards the surface of the anterior pole 60 until the point 32 contacts and slightly punctures the surface of the anterior pole 60. Anchoring the point 32 in this manner allows the instrument 10 to remain in the proper position throughout the procedure, properly positions the cutting edge 38 of the knife 36 so that it has also slightly punctured the surface of the anterior capsule 50, and provides a hold on the portion of the anterior capsule which ultimately will be removed through the limbus incision.

Next, the surgeon manipulates the foot pedal of the fluid control system (not shown) to start the flow of fluid through the passageways 20 and 22 of the main body portion 12 of the instrument 10. As the fluid flows through passageway 20, into the rounded internal chamber 18 and contacts the paddlewheel 24, the paddlewheel 24 begins to rotate, driving the cutting edge 38 of the knife 36 in a continuous and circular path across the surface of the anterior capsule 50. Once the cutting edge 38 of the knife 36 has traveled 360 degrees, the releasable stop 40 prevents further rotation of the knife 36. If desired, the releasable stop 40 can be released via a button (not shown) by the surgeon so that additional cutting will occur. The surgeon can also start and stop movement of the knife 36 via the foot pedal of the fluid control system, if desired.

The central passageway 42 is used for delivery of a viscoelastic solution to the operative field. This fluid is used to maintain an adequate depth of the anterior chamber during a procedure. By maintaining such depth in the anterior chamber, damage to the posterior surface of the cornea is avoided. The optional additional passageway 46 also extends substantially the entire longitudinal length of the main body portion 12 and is used to suction off the capsular membrane and undesired fluid, etc., from the operative field during a procedure. Passageway 42 and the optional additional passageway, like passageways 20 and 22, are remotely operable via the foot pedal and fluid control system.

Figure 3:
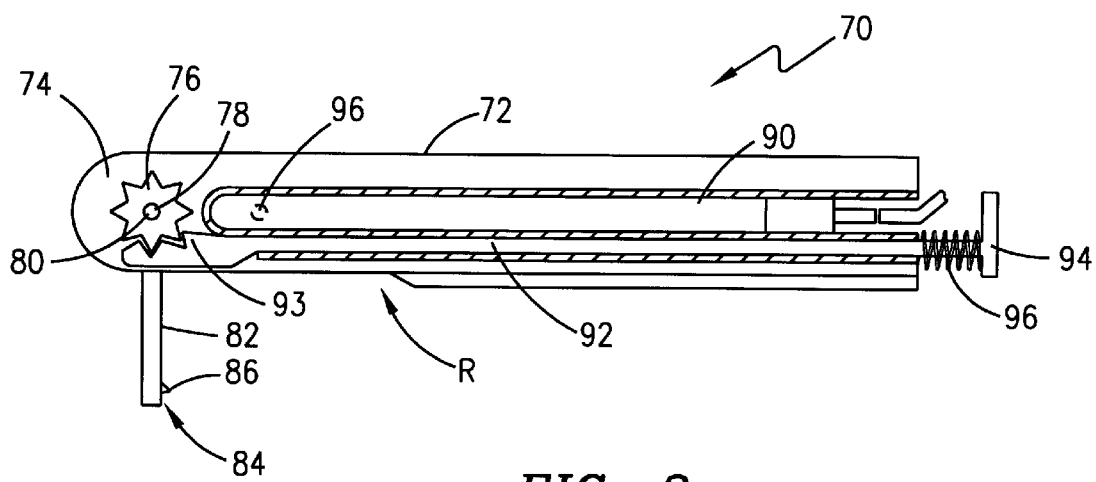
FIG. 3 is a perspective view, partially in section, of a different embodiment of the remotely operable intraocular surgical instrument of the present invention.

Now referring to FIG. 3, a different embodiment of the remotely operable intraocular surgical instrument 70 of the present invention is illustrated. In this embodiment, the main body portion 72 of the instrument 70 also includes at its distal portion a generally rounded internal chamber 74. Within the rounded internal chamber 74 of this embodiment, however, is located a rotatable gear 76. The rotatable gear 76 is attached at its midpoint 78 to an anchor pin 80 which extends through and below the main body portion 72 of the instrument 70. Associated with the anchor pin 80 is an arm 82, a knife 84 and a cutting edge 86. The structure of the anchor pin 80, arm 82, knife 84 and cutting edge 86 are identical to those found in the preferred embodiment described above.

In this embodiment, associated within and running substantially the entire longitudinal length of the main body portion 72 of the instrument 70 are a first defined internal passageway 88 and a second defined internal passageway 90 which connect the proximal end of the main body portion 72 with the rounded internal chamber 74 of the distal end of the main body portion 72. Disposed within the first passageway 88 is a shaft 92 which engages the rotatable gear 76 with specialized teeth 93 at the distal end of the shaft 92 and extends from the proximal end of the main body portion 72 of the instrument 70. The specialized teeth 93 are shaped and positioned so that movement of the shaft 76 towards the distal end of the main body portion 72 is communicated to the rotatable gear 76, but the return movement of the shaft 76 and specialized teeth 93 do not rotate the rotatable gear 76 in the opposite direction. A handle 94 is included at the proximal end of the shaft 92. Preferentially, the handle 94 is disc-shaped to correspond to and receive the thumb or finger of an operator. Optionally, finger grips (not shown) are provided along the exterior proximal end of the main body portion 72 to provide the operator with sufficient grip and manipulation of the instrument 70 during use. A spring 96 disposed between the handle 94 and the proximal end of the main body portion 72 maintains the shaft 92 in a neutral position. Although a spring 96 is disclosed herein, it is noted that any suitable means for maintaining the shaft in a neutral position within the first passageway and returning the shaft, once moved, to said neutral position, may be used, if desired.

In use, as pressure is applied to the handle 94 by the surgeon, the shaft 92 communicates this movement via the specialized teeth 93 to the rotatable gear 76, which, in turn, rotates the anchor pin 80, arm 82, knife 84 and cutting edge 86 of the instrument 70. By fully depressing the handle 94, the surgeon rotates the arm 82, and thus the knife 84, a full 360 degrees. The cutting edge 86 thus makes a continuous and circular cut into the anterior capsule surface (FIG. 6), ultimately producing a circular section of the surface to be removed so that extraction/emulsification can occur. Like the preferred embodiment, the second passageway 90 is used for delivery of a viscoelastic fluid via opening 96 to the operative field. The provision of such a viscoelastic fluid is controlled by a means for fluid control preferably including a foot pedal for remote operation thereof by the surgeon.

Figure 7:
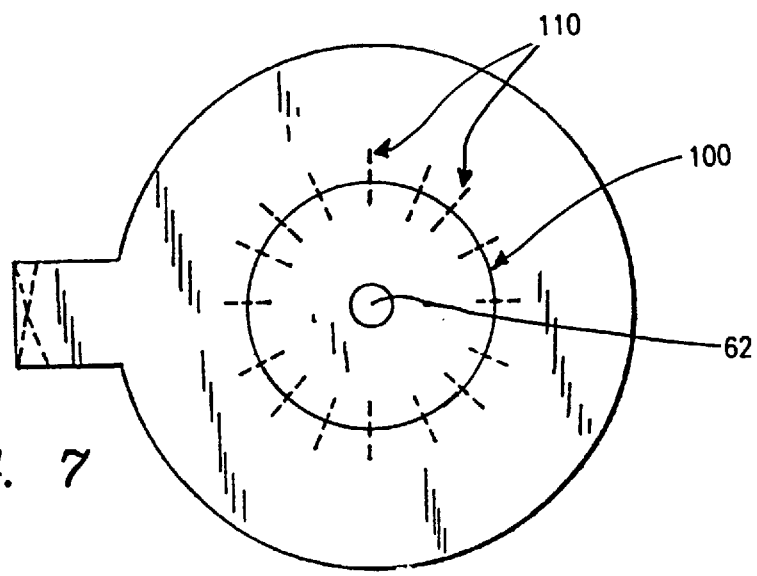
FIG. 7 is a front view of a human eye, illustrating the continuous, smooth, stress-free, tag-free cut made in the anterior capsule by an embodiment of the remotely operable surgical instrument of the present invention.

In FIG. 7, the continuous, smooth, stress-free, tag-free cut 100 made in the anterior capsule by an embodiment of the remotely operable surgical instrument of the present invention is illustrated. As previously discussed, the small tags created by prior art devices and methods can lead to capsular tears which may extend posteriorly to the posterior capsule. Such radial tears constitute a complication because they destabilize the lens, making further cataract removal and safe intraocular lens placement within the lens capsule later in the operation difficult at best.

Like the preferred embodiment, the instrument 70 optionally includes a releasable stop to prevent movement of the knife past 360 degrees. This releasable stop can be remotely released by the surgeon in the event additional cutting is desired. Also like the preferred embodiment, the passageway 90 and the optional additional passageway are used to deliver viscoelastic fluid to the operative field and remove waste and undesired materials (e.g., capsular membrane tissue) from the operative field, respectively.

One of the unique features of the remotely operable surgical instrument of the present invention is the design of the rotating arm 30. With some prior art devices, the cutting edge of the knife is hidden by the body of the instrument such that the surgeon finds it difficult, if not impossible, to visually inspect the cutting edge as it cuts the surface of the anterior capsule. With the unique design of the arm of the present invention instrument, the surgeon can more easily visually inspect the cut being made by the cutting edge of the knife due to the rotating arm being of a sufficient length such that the arc made by the rotating arm extends beyond the main body portion of the instrument. Although the arm, and thus the knife, pass below the main body portion for a small segment of the 360 degree rotation, the large majority of the 360 degrees traveled by the knife occurs beyond away from the main body portion, increasing visibility of and control over the cut being produced by the instrument.

Although the embodiments described herein describe movement of the arm via mechanical means, it is noted that movement of the arm can be accomplished by any suitable means, including without limitation electrical- and hydraulic-based systems.

Another unique feature of the intraocular surgical instrument of the present invention is the simplicity (and thus cost efficiency) of its design. To further that advantage, the main body portion and all other parts, excluding the cutting edge of the knife are preferentially composed of a high impact medical grade plastic, polymer or resin. The instrument and its parts can thus be injected molded, stamped or formed in other ways customary in the art from such a material or materials. Additionally, due to their low cost and ease of manufacture, the instrument is preferably disposable after use, providing obvious medical benefits with respect to contamination and the like.

Yet another unique feature of the intraocular surgical instrument of the present invention is the above-described various arm sizes. Since the instrument can be manufactured with different lengths of arm, the surgeon can tailor the size of the cut to the eye and/or condition of the patient.

It should be noted that any suitable fluid for closed chamber movement can be used with the remotely operable intraocular surgical instrument of the present invention. It should be further noted that passageways of the main body portion of the instrument may be internally defined by the internal structure of the main body portion of the instrument or can be tubes running within internally defined passageways within the main body portion of the instrument.

Although preferred embodiments of the invention have been illustrated in the accompanying drawings and described in the foregoing Detailed Description, it will be understood that the invention is not limited to the embodiments disclosed, but is capable of numerous rearrangements and modifications of parts and elements without departing from the spirit of the invention.

I claim:

1. A remotely operable intraocular surgical instrument specifically adapted for capsulorehexis procedures and capable of producing a continuous, circular, smooth, stress-free, tag-free cut along the anterior capsule to facilitate removal of the lens during a capsulectomy, comprising:

a main body portion having a distal end and a proximal end;

said main body portion including a rounded internal chamber toward its distal end;

said rounded internal chamber having a rotatable paddlewheel located therein, said paddlewheel attached at its midpoint to the main body portion such that said paddlewheel freely rotates around its midpoint;

said paddlewheel also attached at its midpoint to an anchor pin having an upper end and a lower end, said anchor pin extending below the main body portion;

said anchor pin having a sharpened point at its lower end and an arm attached toward the lower end of the anchor pin;

said arm having an outer end and said arm rotatable through an arc which is larger than the distal end of the main body portion;

a knife attached toward the outer end of said arm, said knife including a cutting edge;

a means of attachment of the knife to the arm;

said cutting edge extending slightly below the lower end of the anchor pin;

said anchor pin, said arm, said knife and said cutting edge of said knife all rotatable with said paddlewheel;

said main body portion defining a first and a second internal passageway, said first and said second passageways extending substantially the entire longitudinal length of the main body portion and connecting with the rounded internal chamber of the main body portion toward the distal end of the main body portion;

said first passageway adapted to receive and communicate at least one fluid along its longitudinal length in the direction of the distal end of the main body portion, through the rounded internal chamber, and contacting the paddlewheel, causing the paddlewheel to rotate and thus also causing the anchor pin, the arm and the cutting edge of said knife to rotate, causing the cutting edge of the knife to produce a continuous, circular, smooth, stress-free and tag-free cut;

said second passageway adapted to receive and communicate the at least one fluid from the rounded internal chamber, along its longitudinal length in the direction of the proximal end of the main body portion and expel said at least one fluid from the proximal end of the main body portion; and means for providing to and removing from the main body the at least one fluid.

2. The intraocular surgical instrument of claim 1, further including a first central passageway extending substantially the entire longitudinal length of the main body portion and closed at its distal end, said first central passageway open at its proximal end and including an opening towards its distal end, said first central passageway capable of receiving at least one fluid at its proximal end to be delivered through the first central passageway via the distal opening.

3. The intraocular surgical instrument of claim 2, wherein the at least one fluid delivered by the central passageway is a viscoelastic fluid.

4. The intraocular surgical instrument of claim 2, further including a second central passageway extending substantially the entire longitudinal length of the main body portion and capable of suctioning undesired fluid and material away from an operative field and expelling said undesired fluid and material through the proximal end of the main body portion.

5. The intraocular surgical instrument of claim 1, further including a releasable stop located within a recessed portion below the distal end of the main body portion to prevent rotation of the paddlewheel and associated knife past 360 degrees.

6. The intraocular surgical instrument of claim 5, wherein the releasable stop can be released to allow the knife to cut past 360 degrees.

7. The intraocular surgical instrument of claim 1, wherein the means for providing and removing the at least one fluid to the main body portion includes a recirculation pump.

8. The intraocular surgical instrument of claim 7, further including a foot pedal to control the recirculation pump.

9. A remotely operable intraocular surgical instrument specifically adapted for capsulorehexis procedures and capable of producing a continuous, circular, smooth, stress-free, tag-free cut along the anterior capsule to facilitate removal of the lens during a capsulectomy, comprising:

a main body portion having a distal end and a proximal end;

said main body portion including a rounded internal chamber toward its distal end;

said rounded internal chamber having a rotatable gear located therein, said gear attached at its midpoint to the main body portion such that the gear freely rotates around its midpoint;

said gear also attached at its midpoint to an anchor pin having an upper end and a lower end, said anchor pin extending below the main body portion;

said anchor pin having a sharpened point at its lower end and an arm attached toward the lower end of the anchor pin;

a knife attached to said arm and having a cutting edge extending slightly below the lower end of the anchor pin;

said anchor pin, said arm, said knife and said cutting edge of said knife all rotatable as the gear rotates;

said main body portion defining a first internal passageway extending substantially the entire longitudinal length of the main body portion and connecting with the rounded internal chamber of the main body portion toward the distal end of the main body portion;

said main body portion further defining a second internal passageway extending substantially the entire longitudinal length of the main body portion which is closed at its distal end and includes an upper opening at its distal end;

a shaft having a handle at its proximal end and teeth at its distal end, said shaft disposed within the first passageway and said teeth adapted to engage the gear and communicate motion applied to the handle to the gear, rotating the gear and thus also causing the anchor pin, the arm and the cutting edge of the knife to produce a continuous, circular, smooth, stress-free and tag-free cut; and said second passageway adapted to receive, communicate and deliver at least one fluid from the proximal end of the main body portion to an operative field via the upper opening toward the distal end of the second passageway.

10. The intraocular surgical instrument of claim 9, further including means for preventing rotation of the gear past 360 degrees.

11. The intraocular surgical instrument of claim 10, wherein the means for preventing rotation of the gear past 360 degrees is a releasable stop.

12. The intraocular surgical instrument of claim 11, wherein the releasable stop can be released to allow the gear to rotate past 360 degrees.

13. The intraocular surgical instrument of claim 9, wherein the at least one fluid received, communicated and delivered via the second passageway, is a viscoelastic fluid.

14. The intraocular surgical instrument of claim 9, further including a central passageway extending substantially the entire longitudinal length of the main body portion and capable of suctioning undesired fluid and material away from and operative field and expelling said undesired fluid and material from the proximal end of the central passageway.

15. The intraocular surgical instrument of claim 9, further including means for providing the at least to be fluid to be delivered via the second passageway.

16. The intraocular surgical of claim 15, wherein the means for providing the at least one fluid includes a pump and a foot pedal to control said pump.

17. The introacular surgical instrument of claim 16, wherein the pump is a recirculation pump.

* * * * *